United States Patent [19]

McVicker et al.

[11] Patent Number: 5,763,731
[45] Date of Patent: Jun. 9, 1998

[54] PROCESS FOR SELECTIVELY OPENING NAPHTHENIC RINGS

[75] Inventors: Gary B. McVicker, Califon, N.J.; Michele S. Touvelle; Carl W. Hudson, both of Baton Rouge, La.; David E. W. Vaughan, Flemington, N.J.; Michel Daage, Baton Rouge, La.; Sylvain Hantzer, Prairieville, La.; Darryl P. Klein, Baton Rouge, La.; Edward S. Ellis, Basking Ridge, N.J.; Bruce R. Cook, Pittstown, N.J.; Owen C. Feeley, Clinton, N.J.; Joseph E. Baumgartner, Lebanon Township, N.J.

[73] Assignee: Exxon Research and Engineering Company, Florham Park, N.J.

[21] Appl. No.: 631,472

[22] Filed: Apr. 12, 1996

Related U.S. Application Data

[63] Continuation-in-part of Ser. No. 523,299, Sep. 5, 1995.
[51] Int. Cl.[6] ................................ C07C 5/22; C07C 5/31
[52] U.S. Cl. .................... 585/737; 585/940; 208/65; 208/137
[58] Field of Search ........................... 585/940, 737; 208/65, 137

[56] References Cited

U.S. PATENT DOCUMENTS

| | | | |
|---|---|---|---|
| 3,617,511 | 11/1971 | Jenkins et al. | 585/940 |
| 5,334,792 | 8/1994 | Del Rossi et al. | 585/940 |
| 5,345,026 | 9/1994 | Chang et al. | 585/940 |
| 5,382,730 | 1/1995 | Breckenridge et al. | 585/940 |
| 5,382,731 | 1/1995 | Chang et al. | 585/940 |
| 5,463,155 | 10/1995 | Galperin et al. | 585/737 |

*Primary Examiner*—Walter D. Griffin
*Attorney, Agent, or Firm*—Henry E. Naylor

[57] ABSTRACT

Naphthenic rings in naphthenic ring-containing compounds in a feedstream are selectively opened wherein at least about 50 wt. % of the ring compounds in the feedstream are characterized as containing at least one $C_6$ ring having at least one substituent containing 3 or more carbon atoms. The naphthenic rings are opened without significant dealkylation of any pendant substituents on the ring. The feedstream, containing such compounds, is contacted with a supported catalyst containing a metal selected from Ir, Ru, or a mixture thereof, which catalyst when reacted with a feed comprised of 20 wt. % n-butylcyclohexane in heptane diluent will result in: a) at least a 10% yield of $C_{10}$ paraffin yield/%$C_{10}$ ring disappearance.

43 Claims, No Drawings

PROCESS FOR SELECTIVELY OPENING NAPHTHENIC RINGS

CROSS REFERENCE TO RELATED APPLICATIONS

This is a continuation-in-part of U.S. Ser. No. 08/523,299 filed Sep. 5, 1995.

FIELD OF THE INVENTION

The present invention relates to a process for selectively opening naphthenic rings of naphthenic ring-containing compounds in a feedstream wherein at least about 50 wt. % of the ring compounds in the feedstream are characterized as containing at least one $C_6$ ring having at least one substituent containing 3 or more carbon atoms. The naphthenic rings are opened without significant dealkylation of any pendant substituents on the ring. The feedstream, containing such compounds, is contacted with a supported catalyst containing a metal selected from Ir, Ru, Rh, or a mixture thereof, which catalyst when reacted with a feed comprised of 20 wt. % n-butylcyclohexane in heptane diluent will result in: a) at least a 10% yield of $C_{10}$ paraffins; and b) a selectivity of at least 0.20, which selectivity is defined as %$C_{10}$ paraffin yield/%$C_{10}$ ring disappearance.

BACKGROUND OF THE INVENTION

There is an increasing demand for environmentally friendly hydrocarbons and clean-burning high performance fuels, such as distillate fuels like diesel and jet fuels. Distillate fuels typically contain paraffins, naphthenes, and aromatics. For fuel quality parameters such as cetane, gravity and emissions, paraffins are the most desirable components, followed by naphthenes, followed by aromatics. The least desirable are multi-ring aromatic compounds. While various refinery processes produce distillate fuels, these processes are typically limited in their capability to produce high quality distillate fuel and/or high yields of distillate fuel. For example, conventional hydrogenation processes saturate aromatic rings to naphthenes, thereby increasing the cetane number and increasing the API gravity (lower density). The disadvantage of hydrogenation alone is that naphthenes have generally lower cetane values and are more dense than paraffins having substantially the same number of carbon atoms. The greater density of naphthenes results in reduced volume of the distillate fuel blend relative to a composition containing similar concentrations of paraffins instead of naphthenes. Similarly, multi-ring naphthenes are generally more dense and have lower cetane values than single-ring naphthenes having substantially the same number of carbon atoms. In addition, naphthenes can be converted to aromatics via oxidation reactions. Since combustion of naphthenes in fuels occurs under oxidizing conditions, there is the potential for naphthenes to revert to aromatics under combustion conditions, thus further reducing fuel quality.

Another conventional refinery process for producing distillate fuels is hydrocracking. Hydrocracking catalysts are typically composed of hydrogenation metals supported on acidic supports, such as zeolites. These catalysts are effective, under typical process conditions, for extensive hydrogenation of aromatics and for reducing the number of ring structures, however with the accompanying liability of extensive cracking to lower boiling products including gases which lowers the overall boiling range and limits the volume of final distillate product. In fact, analyses of distillate boiling range paraffin content in hydrocracking feeds versus products suggest little net increase in production of these paraffins via hydrocracking, rather concentration of paraffins in the final product through the cracking of ring structures to lower molecular weight compounds which no longer reside in the distillate boiling range. Thus, the apparent increase in distillate boiling range paraffins and improved distillate fuel quality can result primarily from a combination of hydrogenation of aromatics and a concentration of paraffins in a reduced volume of distillate product.

There is also an increasing demand for low toxicity, biodegradable solvents, of which paraffins are a preferred class. Consequently, it is desirable to reduce the cyclic compound content of hydrocarbon solvent blends, in general, and to convert naphthenes to paraffins, in particular. While there are descriptions of ring opening reactions in the prior art, owing to the increasing demand for more environmentally friendly solvents and clean-burning, high performance fuels, it is highly desirable to have a process which is more selective for ring opening than currently available. Selectivity for ring opening is related to the propensity for cleavage of a ring bond which results in product molecules having an equivalent number of carbon atoms and one less ring than the original molecule, rather than cleavage of a bond which results in a product molecule having fewer carbons than the original molecule. A perfectly selective ring opening process would give only ring bond cleavage to produce molecules having an equivalent number of carbon atoms and one less ring than the original molecule. For example, from a hydrocarbon stream containing only single ring naphthenes of n number of carbon atoms, the product from perfect ring opening selectivity would be only paraffins of n number of carbon atoms.

Thus, the greater number of product molecules from a ring opening process having an equivalent number of carbon atoms and one less ring than the original molecule, the greater the selectivity for ring opening. Greater selectivity for ring opening is important for the reasons that a) the number of ring structures in a product stream will be decreased, b) significant dealkylation of any pendant substituents on the ring, which will reduce the volume of product in a specified boiling range, will be minimized and c) the density of the product stream will be decreased providing volume swell. The present invention provides for a ring opening process, and the criteria for selecting a catalyst for that process, with significantly higher selectivity for ring opening than those practiced in the current art, with the object to decrease the number of ring structures in a product stream and decrease the density of the product stream to improve volume swell, while minimizing dealkylation of pendant substituents to maintain a high volume of product in the desired boiling range.

There are a number of references to ring opening in the the prior art. Most references fall into two general categories—hydrogenolysis and hydrogenation/hydrocracking. "Hydrogenolysis", for purposes of this invention, is defined as cleavage of a carbon-carbon bond, with addition of hydrogen at each point of cleavage. Most references in this category deal with reactions of small, single ring naphthenes over primarily noble metal catalysts. "Hydrogenation/hydrocracking" is generally practiced on larger cyclic molecules over primarily acidic zeolite-supported noble and other Group VIII metal catalysts. The more selective ring opening process of the present invention differs in that the catalyst is selected from those which give higher hydrogenolysis activity and selectivity for ring opening than previously recognized or anticipated. Furthermore, they provide significantly less substituent and secondary product cracking in ring opening than observed in conventional hydrocracking processes.

Much academic research has sought to elucidate key mechanisms controlling product distributions in hydrogenolysis and hydrocracking reactions by using model compounds and specific noble metal catalyst types. Typical studies have been reviewed by Gault (Adv. Catal., 30, 1–95, (1981) with a particular attention to $C_6$ ring isomers, including a description of skeletal isomerization of hydrocarbons over metal catalysts and a discussion of the mechanisms of ring opening reactions. The greater ease for ring opening $C_5$ versus $C_6$ cycloparaffin rings and mechanistic implications related to which bond in the $C_5$ ring is cleaved are described.

The isomerization of $C_6$ ring (cyclohexane) to $C_5$ ring (methylcyclopentane) was demonstrated as a step preceding ring opening (the pentyl-ring opening much faster than the hexyl-ring) by Schultz and co-workers (Proc. 5th Intl. Catal. Congr., North-Holland Publ. (Aidam), v.2, 1229–39, (1973)). The tendency for side chains on ring structures to fragment and to isomerize methyl groups to other ring sites (the so called "paring" reaction) has also been demonstrated (Egan, et al. J. Amer. Chem. Soc., 84, 1204–12, (1962). The latter process, which results in tertiary carbon atoms on the ring, severely inhibits ring opening at those sites and is in agreement with the findings of Gault. These processes are characteristic of those using a wide range of bifunctional metal hydrogenation-acidic catalysts. For instance, various Pt-cation exchanged acidic zeolites have been demonstrated to be effective for naphthene isomerizations using cycloparaffins with short side chains (Weitkamp, et al, in "Structure and Reactivity of Modified Zeolites", Elsevier (Adam), 279–90, (1984)). Such naphthene isomerizations are also well demonstrated on non-noble metal, non-zeolite catalysts (NiS on amorphous silica-alumina) for longer side-chain $C_9$ to $C_{12}$ alkyl-napthenes (Egan, et al, J. Amer. Chem. Soc., 84, 1204–12 (1962)). To meet distillate quality targets, control of the paring isomerizations and subsequent dealkylations are particularly important in order to limit the number of lower cetane, highly branched paraffins which may result following ring-opening.

Other references to ring opening include U.S. Pat. No. 3,617,511 which teaches a catalyst comprised of rhodium or ruthenium on an acidic refractory oxide, specifically a halogen-promoted alumina, for ring opening of cycloparaffins. Greater selectivity for ring opening methylcyclopentane (MCP) versus cyclohexane (CHX) in admixture was observed. In addition, essentially sulfur free feeds were preferred.

Further, U.S. Pat. Nos. 4,783,575 and 4,834,866 disclose the use of a chlorided platinum-alumina catalyst to isomerize $C_4$–$C_6$ paraffins to more highly branched isomers and to ring open cycloparaffins found in the feedstock. Continuous addition of chloride to maintain catalyst acidity and low severity conditions to minimize secondary cracking were preferred. Platinum was found to be most suitable of the catalytic metals.

Also, U.S. Pat. No. 3,631,117 describes a process for the hydroisomerization of cyclic hydrocarbons, specifically isomerization of $C_6$ ring cycloparaffins to $C_5$ ring isomers, employing a zeolite-supported Group VIII metal catalyst for hydroisomerization of cyclics. A broad range of Group VIII metals alone or in combination with each other or with tungsten are claimed. Notably, iridium was absent from this group. The conditions for this hydroisomerization process also provided some ring opening and paraffin isomerization. A note of caution was made that excessive hydrocracking (reducing the number of carbon atoms from the original cyclic molecule) can be a problem under the conditions of $C_6$ ring to $C_5$ ring hydroisomerization.

The sensitivity for cracking of a n-butyl side chain from a $C_5$ ring with platinum on carbon catalysts has been noted (Sergienko, et al., Khim. Geol. Nauk 2, 65–70 (1976)). At relatively mild conditons (225° C. to 270° C.) low yields of $C_9$ paraffins were produced with good selectivity. However, as conversion increased, through either higher platinum loadings or higher temperature, significant amounts of hydrocracking and aromatic products were formed.

There are also patents which teach ring opening in naphtha feeds. For example, U.S. Pat. No. 5,334,792 discloses a two stage process wherein a naphtha feedstock is reacted in a first stage with a zeolite catalyst containing a hydrogenation component under conditions which will saturate aromatics, such as benzene, and open cyclic hydrocarbons. The reaction product from the first stage is passed to a second stage containing an isomerization catalyst to isomerize paraffins to obtain higher octane products. Also, process of U.S. Pat. No. 5,345,026 comprises contacting cyclic hydrocarbons with a catalyst under sufficient ring opening conditions wherein the catalyst is comprised of: (i) a hydrogenation/dehydrogenation component; and (ii) an acid component comprised of a Group IVB metal oxide modified with an oxyanion of a Group VIB metal.

While hydrocracking can reduce the number of ring compounds in the final distillate product with an attendant increase in the cetane number, the yield of product boiling in the distillate range is significantly reduced by excessive cracking to lower boiling products, including gases. One reason for excessive cracking is that paraffins and paraffinic side chains derived from previously ring opened naphthenes, crack more readily than the starting and remaining napthenes. Comparative analyses of distillate boiling range paraffin contents in both hydrocracking feeds and the resulting products suggests little net increase in paraffins, but rather a concentration of such paraffins in the final product because products from secondary cracking of the opened naphthene rings end up in a lower boiling fraction, outside of the distillate range. Thus, the apparent increase in distillate paraffins, and thus improved distillate fuel quality results primarily from a combination of aromatics saturation and a concentration of paraffins in a reduced volume of product within a given boiling range.

Most recent developments in hydrocracking catalysts have focused on matching the hydrogenation of catalytic noble metals with an acid cracking function. The acid function was provided in earlier catalysts by an amorphous alumina or silica-alumina, and more recently by a crystalline zeolite. The metal function is typically provided by Pt and/or Pd, although all noble metals are treated as functionally equivalent in the patent art. The zeolite component is typically a modified Y-type (U.S. Pat. No. 3,130,007), usually derived from a steamed variety designated "ultrastable-Y", or simply US-Y (U.S. Pat. No. 3,449,070). The art comprises numerous combinations of these two "matched" components, most of which were recently reviewed by Ward (Fuel Process. Technol., 35, 55–85 (1993)) who described in detail the manipulation of product slates by changing catalysts. Key differentiating characteristics are in the variable combinations of Pt and Pd (one or both metals, relative loading, dispersion, distribution between zeolite and matrix) and the particular way in which the US-Y has been processed. The latter components are usually defined by low unit cell values, high Si/Al ratios, residual exchange cation contents and sometimes pore volumes. This last property is determined by the methods and intensity for dealuminating which determines the distribution of mesopores within the remnant zeolite crystal and the retained crystalline micropore volume. Ward (ibid) has authoritatively reviewed the many differences in selectivities between the zeolite products of these numerous process variations.

Attempts have been made to increase hydrocracking selectivity via hydrodecyclization. For example, European Patent Application EP0512652 A1 describes a "hydrodecyclization" process wherein the distillate fuel is contacted at elevated temperatures with a suitable catalyst in the presence of hydrogen, which catalyst is comprised of one or more Group VIII noble metals on a modified Y-type zeolite support having a unit cell size between 24.20 Å and 24.40 Å and a SiO2/Al2O3 molar ratio of 10 to 150. Similarly, European Patent Application EP05 19573 Al teaches a process for reducing cyclic structures similar to the above EP application except that an alkali or alkaline-earth metal is also present. The objective was to improve the cetane number of distillate fuels by opening rings (hydrodecyclization) without excessive cracking. While these two European patent applications suggest that ring opening is taking place, there is no direct evidence in said applications to show that selective ring-opening is the reason for improved distillate product quality. Based on process conditions and product yields and qualities provided in the examples, it is more likely that the reported increase in distillate boiling range paraffins and improved distillate fuel quality results primarily from a combination of extensive hydrogenation of aromatics and a concentration of paraffins in a reduced volume of product.

This is in agreement with the observations of Mignard, et al., who studied the opening of naphthenic molecules over a platinum on Y zeolite catalyst under hydrocracking conditions ("Catalytic and Hydroprocessing of Petroleum and Distillates," M. Decker (New York), 447–459 (1994)). The reaction pathway for ring opening of cycloparaffins was described as sequential isomerization of $C_6$ to $C_5$ ring, followed by carbon-carbon bond cleavage to give ring opening, followed by rapid cracking via additional carbon-carbon bond cleavage reactions. The results showed cracking propensity increases with increasing carbon number and that ring opened products are highly susceptible to further cracking. The conclusion reached was that ring opening selectivity to minimize cracking is difficult to control. Indeed these authors suggest that the present state of the art is representative of the limits inherent in the competing reactions involved in hydrocracking under the allowable process conditions.

Hydrocracking catalysts are bifunctional in nature, containing both metal and acidic functionalities. Balancing the relative activity of these functions is of major importance in maintaining high productivity and selectivity. State of the art hydrocracking catalysts are generally dominated by an acid component. Acid catalyzed chemistry is initiated by a metal function in such catalysts by generating olefinic intermediates from paraffinic or cycloparaffinic precursors. There is general concensus in the literature that Group VIII metals are essentially equivalent for this purpose. The dominance of the acid function can lead to excessive cracking since primary products arising from ring opening are highly susceptible to acid cracking routes to lower molecular weight products. Thus, the primary focus on improving the performance of these bifunctional hydrocracking catalysts has been on optimizing the acid function. For these reasons, it remains difficult to control excessive cracking even in state of the art catalysts.

To maintain molecular weight of the products and to reduce volume of lower molecular weight fractions, the cleaving of side chains from ring compounds by the acid component needs to be minimized. Recent attempts to control acidity in zeolites include lowering of acidity with cation titration of residual acid sites. However, the approach to low acidity catalysts via dealumination of Y-type reaches a point of diminishing returns because excessive processing, such as multiple steam treatments, exchanges and Al extractions, which are needed to achieve the desired materials, results in major yield and crystallinity losses. Thus cation exchange is an alternate and simpler way to control acidity (though not as efficient or stable as control of Si/Al). Methods for controlling acidity have included ammonia titration in the process stream to exchange proton sites (PCT WO/92/13045), base exchange with alkali and alkali earth cations (Euro. Pat. Appl 0,519 573 A1) and re-alumination exchange methods developed by Lutz (Cryst. Res. Technol., 25, 921–6, (1990)) and others (PCT WO/93/25477).

Therefore, there is still a need in the art for a more selective ring opening process which can meet the objectives of: (i) reducing the number of ring structures in a product stream; (ii) avoiding significant dealkylation of any pendant substituents on the ring which reduces the volume of product in a specified boiling range; and (iii) increasing volume swell by lowering the density of the product stream.

SUMMARY OF THE INVENTION

In contrast to the prior art, we have found that significant enhancements in ring opening selectivity are made by focusing on the metal function of the bifunctional catalyst. Contrary to the teachings of the prior art, we have found that all Group VIII metals are not equivalent for ring opening activity and selectivity. By focusing on the hydrogenolysis activity of these Group VIII metals, we have discovered that Ir, Ru, and Rh have exceptional activity and selectivity for the target reaction of selective ring opening. Further, we have found that additional enhancements in performance can be obtained by coupling this dominant hydrogenolysis activity with an effective, subordinate amount of controlled acidity.

In accordance with the present invention, there is provided a process for selectively opening rings of ring compounds in a feedstream wherein at least about 50 wt. % of the ring compounds in the feedstream are characterized as containing at least one $C_6$ ring having at least one substituent containing 3 or more carbon atoms, which substituents are selected from the group consisting of fused 5-membered rings; fused 6-membered rings; $C_3$ or greater alkyls, cycloalkyls; and aryl groups, which process comprises contacting said feedstream with a catalyst component in the presence of hydrogen at a temperature from about 150° C. to about 400° C., a total pressure of 0 to 3,000 psig, which catalyst is comprised of an effective amount of a metal selected from Ir, Ru, Rh, and mixtures thereof, on a catalyst support, which catalyst when reacted with a feed comprised of 20 wt. % n-butylcyclohexane in heptane diluent, at a temperature of 150° C. to 350° C., a hydrogen treat rate of 2,000 standard cubic feet per barrel on liquid feed, a total pressure of 500 psig, and a liquid hourly space velocity of at least 5 on liquid feed, will result in: a) at least a 10% yield of $C_{10}$ paraffins; and b) a selectivity of at least 0.20, which selectivity is defined as %$C_{10}$ paraffin yield/%$C_{10}$ ring disappearance.

In a preferred embodiment of the present invention the catalyst, when reacted with the 20 wt. % n-butylcyclohexane in heptane diluent, will result in: a) at least a 15% yield of $C_{10}$ paraffins; and b) a selectivity of at least 0.30; more preferably at least a 20% yield of $C_{10}$ paraffins at a selectivity of at least 0.04.

In another preferred embodiment of the present invention the amount of metal is from about 0.01 to about 3 wt. %, based on the total weight of the catalyst.

In still another preferred embodiment of the present invention the catalyst contains an effective amount of one or more performance enhancing transition metals, which transition metal is preferably selected from the 4th, 5th, and 6th periods of the Periodic Table of the Elements.

In yet another preferred embodiment of the present invention the catalyst support contains an effective amount of acidic function so as to promote isomerization, but not so much as to cause an undesirable degree of severance of any side groups on the ring.

DETAILED DESCRIPTION OF THE INVENTION

The present invention is practiced on feedstreams containing ring compounds wherein at least 50% of the ring compounds contain at least one $C_6$ ring having at least one substituent containing 3 or more carbon atoms, which substituents are selected from the group consisting of fused 5-membered rings, fused 6-membered rings, $C_3$ or greater alkyl and cycloalkyl groups, and aryl groups.

Preferred feedstreams on which the present invention is practiced include those containing such compounds, preferably those boiling in the distillate range (about 175° C. to 400° C.). Non-limiting examples of such feedstocks include diesel fuels, jet fuels, and heating oils. Preferably these feedstocks have been hydrotreated to reduce sulfur content to low levels, preferably less than 100 ppm, more preferably below 10 ppm. Other feedstreams can also be treated in accordance with the present invention by the manipulation of catalyst and process conditions. Such other feedstreams include chemical feedstocks, and lube streams.

The instant process will impact the characteristics of these feedstocks by: (i) reducing number of ring structures in the product stream; (ii) avoiding significant dealkylation of any pendant substituents on the ring which reduces the volume of product in a specified boiling range; and (iii) increasing volume swell by lowering the density of the product stream. It is also desirable to produce distillate fuels with cetane numbers in excess of about 40, preferably in excess of about 45, and more preferably in excess of about 50. The cetane number is directly related to the types of molecules that are found in the distillate fuel. For example, the cetane number of molecules within a class (e.g. normal paraffins) increases with the number of carbon atoms in the molecule. Further, molecular classes may be ranked in terms of their cetane number for a specific carbon number: normal paraffins have the highest cetane number, followed by normal olefins, followed by isoparaffins, and followed by monocyclic naphthenes. Aromatic molecules, particularly multi-ring aromatics, have the lowest cetane numbers.

For example, naphthalene has a cetane blending number of about 5 –10; tetrahydronaphthalene (tetralin) about 15, decahydronaphthalene (decalin) about 35–38, butylcyclohexane about 58–62, and decane about 72–76. These cetane measurements are consistent with the trend for higher cetane value with increasing ring saturation and ring opening.

Further, the aromatics content of a distillate stream will vary depending on its source. For example, if the distillate stream is a product fraction from a crude distillation tower, then the stream will be relatively low in aromatics, particularly multi-ring aromatics, and have a relatively high cetane number. Distillate streams which are product fractions from a fluid catalytic cracker, on the other hand, have relatively high amounts of aromatics, particularly multi-ring aromatics, and consequently have relatively low cetane numbers. It is known by those having ordinary skill in the art that an increase in cetane number and cetane index may correspond to an increase in API gravity. Consequently, it is highly desirable to reduce the number of rings by selective ring opening.

Three terms commonly used in the literature to describe the transformation of naphthenes to paraffins or to naphthenes containing fewer rings, are "hydrogenolysis", "hydrodecyclization", and "ring opening". Hydrogenolysis reactions are those in which there is cleavage of a carbon-carbon bond, with addition of hydrogen at each point of cleavage. Hydrodecyclization is more specific in that a cyclic structure is cleaved in a hydrogen environment. Such reactions occur in the hydrocracking of large organic molecules, with formation of fragments that react with hydrogen in the presence of a suitable catalyst and at relatively high temperatures. Such fragments are typically either molecules in which rings have been cleaved, or are alkyl substituents which have been cleaved, or both. This results in products which contain fewer carbon atoms than the original molecule. This of course results in lower boiling products. "Ring opening" can simply be another way to describe hydrodecyclization. However, for purposes of the present invention, selective ring opening means a high propensity for cleavage of a ring bond which results in product molecules having substantially the same number of carbon atoms and one less ring than the original molecule.

The literature regarding the above terms are typically based on two types of experimental data—real feed data and model compound data. Examples of feeds on which data is reported in the literature include hydrogenated streams containing cyclic structures, such as hydrocracked products, aromatic hydrogenation products, and deasphalted oils. Streams which contain predominantly aromatics need to be hydrogenated first. Experimental data cited in the art for real feeds usually refer to the disappearance of rings in the products of interest for a particular process, or for total liquid product recovered. Because of the lack of appropriate analytical techniques and characterization tools, the reaction pathways and mechanisms leading to the disappearance of rings cannot be clearly identified and quantified. However, it is common in such reactions that there has been a substantial reduction in boiling point and/or average molecular weight of the product. Boiling point reduction and molecular weight reduction are evidence of non-selective ring-opening. That is, characteristics of alkyl substituents to the ring being cleaved, or cleavage of ring-opened products, or both. There is a substantial amount of literature on ring opening of model compounds, but it is typically limited to simple ring compounds having an alkyl group of only one or two carbon atoms. For example, the majority of experimental data is based on the conversion of methylcyclopentane, cyclohexane, and methylcyclohexane. Only a relatively small amount of data are based on the conversion of compounds having longer carbon substituent groups, such as butylcyclohexane, dimethyl- and trimethylcyclopentane.

Hydrogenolysis, as described in the present invention, is a key pathway for ring opening. Hydrogenolysis of naphthenes can be essentially described by the following two reactions: (1) the breaking of endocyclic carbon-carbon bonds; and (2) the breaking of exocyclic carbon-carbon bonds. The breaking of an endocyclic bond, as in ring opening, leads to a paraffin of same carbon number for a one ring naphthene, or an alkylated naphthene of same number of carbon atoms containing one less ring for a multiring naphthene. The breaking of an exocyclic carbon-carbon bond, as in dealkylation, results in the loss of an alkyl substituent which produces a decrease of molecular weight by producing two molecules of much lower boiling points.

Recognizing that the two reactions may occur co-currently or consecutively, it becomes necessary to define the concept of selective and non-selective ring opening and dealkylation. That is, selective ring-opening without substantial dealkylation of alkyl substituents on the ring, and non-selective ring-opening wherein ring-opening is accompanied by substantial dealkylation of ring substituents. For that reason, it is necessary for choosing a selective ring opening catalyst to use a model compound such as butylcyclohexane which contains both a ring and a substituent containing a significant number of exocyclic carbon atoms. It is difficult to determine if a catalyst is selective for opening the ring as opposed to severing the alkyl substituent for cyclic compounds containing a substituent without a significant number of exocyclic carbon atoms, for example, methylcyclohexane. On the other hand, it is relatively easy to determine whether a catalyst is selectively opening the ring and not severing the substituent on compounds such as butylcyclohexane, which contain a ring substituent having 3 or more carbon atoms.

While preferred catalysts of the present invention will directly open six-membered naphthenic rings, it is preferred that the catalyst system used herein contain an acid function which is effective for isomerizing six-membered naphthenic rings to five-membered naphthenic rings. This is because the ring opening function of the catalysts of the present invention are more active in opening five-membered naphthenic rings relative to opening six-membered naphthenic rings.

The instant process can be practiced by contacting a suitable feedstream with a catalyst of the present invention by any one of several process schemes. For example, in one process scheme the feedstream is contacted with a selective ring opening catalyst of the present invention which contains both a metal hydrogenolysis function and an acid isomerization function, under suitable process conditions. Use of such a catalyst will cause isomerization of $C_6$ naphthenic rings to $C_5$ naphthenic rings as well as selective ring opening of both $C_6$ and $C_5$ rings, with $C_5$ naphthenic ring opening being the predominant ring opening reaction. Suitable process conditions include temperatures from about 150° C. to about 400° C., preferably from about 225° C. to about 350° C.; a total pressure from about 0 to 3,000 psig, preferably from about 100 to 2,200 psig; more preferably about 100 to 1,500 psig; a liquid hourly space velocity of about 0.1 to 10, preferably from about 0.5 to 5; and a hydrogen treat gas rate of 500–10,000 standard cubic feet per barrel (SCF/B), preferably 1000–5000 SCF/B.

Catalysts suitable for use in the present invention which contain both a metal function and an acid function include those comprised of an effective amount of a metal selected from Ir, Ru, Rh, and mixtures thereof, preferably Ir, and Ru, and more preferably Ir; and an effective amount of acidic isomerization function which will cause isomerization of $C_6$ naphthenic rings to $C_5$ naphthenic rings, but not cause excessive cleavage of substituents on the ring. An effective amount of metal would be that amount required to effect ring opening of $C_6$ and $C_5$ naphthenic rings. Typically, such an effective amount of metal would be up to about 10 wt. %, based on the total weight of the catalyst. Preferably the amount of metal will be from about 0.01 wt. % to about 5 wt. %, more preferably from about 0.02 wt. % to 3 wt. %, and most preferably from about 0.1 wt. % to 1 wt. %. An effective amount of acid function would be that amount needed to cause isomerization of $C_6$ naphthenic rings to $C_5$ naphthenic rings, but not so much as to cause excessive cleavage of substituents from the ring and secondary cracking. The precise amount of acidity to balance isomerization versus cleavage of ring substituents depends on many factors, such as the molecular make-up of the feed, the process conditions, and the particular catalyst employed. Thus, it is more practical to define the catalysts of the present invention which are suitable for selective ring opening in terms of meeting certain minimum requirements with respect to paraffin yield and selectivity through a specific catalyst selection procedure. For example, catalysts suitable for the practice of the present invention are those which when reacted with a feed comprised of 20 wt. % n-butylcyclohexane in heptane diluent, at a temperature of 150° C. to 350° C., a hydrogen treat rate of 2,000 standard cubic feet per barrel on liquid feed, a total pressure of 500 psig, and a liquid hourly space velocity of at least 5 on liquid feed, will result in a) at least a 10% yield of $C_{10}$ paraffins and b) a selectivity to $C_{10}$ paraffin products, as defined by (%$C_{10}$ paraffin yield/%$C_{10}$ ring disappearance), of at least 0.20 at any $C_{10}$ ring disappearance level.

In yet another embodiment of the present invention, the acidic function is supplied by a zeolitic material, preferably of the faujasitic type having an Si/M ratio of at least about 30, more preferably greater than about 60, wherein M is selected from the group consisting of Al, Ga, B, Zn, Re, and Cr cations, or mixtures thereof. Such materials are preferably derived from as synthesized materials having Si/M ratios greater than about 4 (i.e., not derived from Y-type (U.S. Pat. No. 3,130,007) or US-Y (U.S. Pat. No. 3,293, 192). Such "as synthesized" high silica starting materials include compositions comprising structures characteristic of faujasite, "Breck-6", and mixtures of the two. Such end members and their mixtures have been reviewed in U.S. Pat. No. 5,116,590. They include those designated ECR-4 (U.S. Pat. No. 4,714,601), ECR-30 (U.S. Pat. No. 4,879,103), ECR-32 (U.S. Pat. No. 4,931,267), ECR-35 (U.S. Pat. No. 5,116,590), ZSM-3 (U.S. Pat. No. 3,415,736), ZSM-20 (U.S. Pat. No. 3,972,983), and variously named analogs of such zeolites, such as EMC-1 and EMC-2 (Delprato et al., Zeolites, 10, p.546–52 (1990)), EMT, "hexagonal faujasites" and others. Such end members and their mixtures have been additionaly reviewed by Treacy et al. (Proc. Roy. Soc. (London), A, (1995)). The preparation of these converted high silica materials are described in co-pending patent application, Attorney Docket No. HEN9515, filed on the same date of the instant application, and incorporated herein by reference. As the "as synthesized" materials can be made with Ga, B, Zn, Fe, and Cr by replacing all or part of the more conventional Al, M may be one or more of these cations, preferably Al. When a zeolite is used as the acid function the most more preferred metal function in comprised of about 0.01 wt. % to 3 wt. % of a Group VIII noble metal selected from the group consisting of Ir, Ru, Rh, and mixtures thereof.

The stream containing the $C_6$ naphthene ring compounds can also be contacted, at reaction conditions, with a mixed catalyst system. That is, with a catalyst system containing two distinct types of catalyst particles. One type of catalyst particle would contain an effective amount of acid isomerization function and the other type of catalyst particle would contain the ring-opening, or metal hydrogenolysis function. As previously stated, the preferred ring-opening function is provided by a metal selected from Ir, Ru, and Rh, more preferably selected from Ir and Ru, and most preferably Ir. The $C_6$ ring-containing stream can also be treated in a staged process. That is, in a first stage wherein it is contacted with a catalyst containing the acid function to cause isomerization of $C_6$ naphthenes to $C_5$ naphthenes, then followed by a second stage wherein the product stream of the first stage, now rich in $C_5$ ring compounds, is contacted with the catalyst containing the ring opening, or metal function. One advantage of a staged process is that reaction conditions can be varied from one stage to the other.

The selective ring opening catalysts of the present invention can also include an effective amount of at least one performance enhancing transition metal, preferably those selected from the 4th, 5th, and 6th periods of the Periodic Table of the Elements. The Periodic Table of the Elements referred to herein is the type found on the last page of *Advanced Inorganic Chemistry*, by Cotton and Wilkinson, Interscience Publishers, 2nd Edition, 1966. Non-limiting examples of such metals include Cu, Zn, Ni, Pt, Re, Co, Mn, Mo, and W. Such performance enhancements include such things as sulfur protection, enhanced metals dispersion of the primary metal (Ir, Ru), and enhanced dehydrogenation activity.

If aromatics are present and need to be saturated, any suitable hydrotreating process can be used to hydrogenate the aromatic rings, so long as it is not associated with excessive cracking. Typical hydrotreating catalyst are comprised of at least one Group VIII metal and a Group VI metal on an inorganic refractory support, preferably alumina or an alumina-silica support. Said Groups are from the Periodic Table of the Elements. The Group VIII metal is present in an amount ranging from about 2 to 20 wt. %, preferably from about 4 to 12 wt. %. Preferred Group VIII metals include Co, Ni, and Fe; with Co and Ni being more preferred. The preferred Group VI metal is Mo, which is present in an amount ranging from about 5 to 50 wt. %, preferably from about 10 to 40 wt. %, and more preferably from about 20 to 30 wt. %. All metal weight percents are based on the total weight of the catalyst. Typical hydrotreating conditions for distillate feedstocks include temperatures from about 200° C. to 400° C., pressures from about 100 to 1500 psig, space velocities from about 0.4 to 6 V/V/Hr, and hydrogen gas rates from about 200 to 6000 standard cubic feet per barrel (SCF/B).

The following examples are presented for illustrative purposes only and are not to be taken as limiting the present invention in any way.

EXAMPLES

Catalyst Selection Procedure

The following experimental procedure was used to select catalysts of the present invention which afford selective ring opening without excessive cleavage of substituent groups on the ring or product paraffins. The feedstock was prepared by dissolving 20 wt. % n-butylcyclohexane (BCH) in heptane, contained 0.140 g. or 0.177 mL of BCH/mL at a density of 0.698 g/mL. The feedstock was filtered and delivered through a small positive-displacement pump to the test reactor run in a fixed-bed, downflow mode under essentially vapor phase conditions. Catalysts tested were of a particle size ranging from about 14–35 mesh to about 80–150 mesh. Product effluent passed from the reactor through a back pressure regulator, exiting at atmospheric pressure. The liquid product was cooled and analyzed by gas chromotography and/or a combination of gas chromatography and mass spectrometry. The yield and conversion results (shown in the tables of results for the examples) were used to establish catalyst activity and selectivity parameters in the following manner.

%BCH Conversion=((g BCH in Feed–g BCH in Product) /g BCH in Feed)×100=% BCH Conversion %$C_{10}$ Paraffin Yield (PY)=(g $C_{10}$ Paraffins in Product/g BCH in Feed)×100

%$C_{10}$ Ring Disappearance (RD)=(g BCH in Feed–(g BCH in Product+g $C_{10}$ Cycloparaffins in Product))/g BCH in Feed)×100

Selectivity for Ring-Opening (R-O)=(%PY/%RD) %$C_{10}$ Paraffin Yield/%$C_{10}$ Ring Disappearance Example 1

(0.9 wt. % Ir/$Al_2O_3$)

A catalyst of this invention was prepared in the following manner, which is known in the art to give a well-dispersed metal catalyst (see U.S. Pat. No. 4,302,359). The outlet of a large fritted-glass filtration funnel was equipped with a $CO_2$ gas delivery tube allowing the gas to flow upward through the glass frit. Into the funnel were placed 375 ml of de-ionized water and 250 g of reforming grade alumina extrudates. The $CO_2$ was bubbled through the mixture for 30 min. An Ir-containing stock solution was prepared by the dissolution of 42.9 g of chloroiridic acid hexahydrate in 1 l. of de-ionized water. The stock solution contained 16 mg Ir/ml and 18 mg Cl/ml. To the extrudate/water mixture was added 141 ml of Ir stock solution, and the passage of $CO_2$ was continued for 4 hr. The aqueous layer was decanted and the catalyst was dried overnight at room temperature (about 22° C.) on a bed of paper towels. The catalyst was subsequently dried under vacuum at 100° C. for 4 hr. prior to being calcined in flowing air at 400° C. for 3 hr. The resulting catalyst was 0.9 wt. % Ir on alumina.

A portion, 0.8 g (1.3 mL), of this 0.9 wt. % Ir/$Al_2O_3$ catalyst was tested for selective ring-opening using the Catalyst Selection Procedure (described above). The results, Table 1, clearly show that the catalyst of Example 1 meets the minimum range of criteria for selective ring opening of the present invention (13.6% paraffin yield at a selectivity (%PY/%RD) of 0.39) at 275° C.

Example 2

(0.9 wt. % Pt /$Al_2O_3$)—Comparative

A catalyst was prepared in a similar manner to that described in Example 1, except that chloroplatinic acid was used instead of chloroiridic acid, which resulted in a catalyst comprised of about 0.9 wt. % Pt on alumina.

This catalyst was tested for selective ring-opening as described for Example 1. The results, by comparison with Example 1 in Table 1, show that 0.9 wt. % Pt/$Al_2O_3$ does not meet the minimum range of requirements of the present invention, and thus is not a catalyst of this invention.

TABLE 1

Comparison of Ring Opening Activity and Selectivity for Catalysts of Examples 1 and 2

| Example | Catalyst | Temp °C. | Tot. LHSV | BCH Conv. | % $C_{10}$ RD | % $C_{10}$ PY | Select- ivity |
|---|---|---|---|---|---|---|---|
| 1 | 0.9% Ir/ $Al_2O_3$ | 275 | 6.0 | 38.4 | 35.2 | 13.6 | 0.39 |
| 2 | 0.9% Pt/ $Al_2O_3$ | 275 | 7.2 | <1.0 | <1.0 | 0.0 | 0.00 |

These results clearly show the difference in ring opening activity and selectivity for iridium versus platinum, supporting the unexpected finding by the inventors hereof that all Group VIII metals, even the Group VIII noble metals, are not equivalent for ring opening activity and selectivity.

Example 3
0.9 wt. % Ir/Dealuminated Y Zeolite (Si:Al=37)—Comparative

A commercial steam dealuminated, extracted, high silica Y zeolite material, unit cell size 24.30 and Si/Al=37, was formed into a support extrudate with 20% alumina binder. This type of catalyst is typically used for hydrocracking in the petroleum industry. The extrudates (⅛ inch) were impregnated with Ir metal in the following manner. The support was dried in a 120° C. oven prior to incipient wetness impregnation. After wettability was determined, an aqueous impregnation solution of the appropriate volume was prepared from a standard solution of chloroiridic acid containing 0.1204 g/mL of Ir. The impregnating solution was added to the support at once with constant stirring to assure homogeneous distribution of the metal. After stirring for 20 minutes, the impregnated material was dried in an oven overnight at 120° C. The dried material was calcined (in air) wherein the temperature was ramped at 1° C./min from room temperature to the final calcination temperature, 270° C.

This catalyst was tested for selective ring-opening as described for Example 1, and the results are shown in Table 2. This catalyst does not meet the minimum range of criteria of the present invention, and thus is not a catalyst of this invention.

Example 4
0.9 wt. % Pt/Dealuminated Y Zeolite (Si:Al=37)—Comparative

A catalyst was prepared via the procedure in Example 3 (above), except that chloroplatinic acid was used instead of chloroiridic acid.

This catalyst was tested for selective ring-opening as described for Example 1, and the results are shown in Table 2 below. This catalyst does not meet the minimum range of criteria of the present invention, and thus is not a catalyst of this invention.

Example 5
0.4% wt. % Pt-0.25 wt. % Pd/Dealuminated Y Zeolite (Si:Al=37)—Comparative A solution containing 30 mL of toluene, 0.179 g. of bis9acetylacetonate palladium II) and 0.231 g. of bis (acetylacetonate platiunum II) was alurried with 25 g. of the zeolite-alumina extrudates described in Example 3 hereof. After stirring every 10 minutes for one hour, the mixture was allowed to stand overnight. The toluene portion was decanted and the extrudate particles were dried, first at room temperature, then at 110° C. for 2 hours. The resulting catalyst was calcined in flowing air at 350° C. for 2 hours.

This catalyst was tested for selective ring-opening as described for Example 1, and the results are shown in Table 2, below. This catalyst does not meet the minimum range of criteria of the present invention, and thus is not a catalyst of this invention.

TABLE 2

Comparison of Ring Opening Activity and Selectivity for Catalysts of Examples 3, 4 and 5

| Example | Catalyst | Temp °C. | Tot. LHSV | BCH Conv. | % $C_{10}$ RD | % $C_{10}$ PY | Select- ivity |
|---|---|---|---|---|---|---|---|
| 3 | 0.9% Ir/ Deal. Y Zeolite | 275 | 4.7 | 98.2 | 76.0 | 11.9 | 0.16 |
| 4 | 0.9% Pt/ Deal. Y Zeolite | 275 | 5.0 | 85.0 | 15.0 | 0.0 | 0.00 |
| 5 | 0.4% Pt— 0.25% Pd/ Deal. Y Zeolite | 275 | 4.8 | 96.2 | 15.2 | 0.0 | 0.00 |

The results for these bifunctional, hydrocracking type catalysts illustrate two points relating to the present invention. First, platinum and a combination of platinum and palladium are ineffective for selective ring opening and thus, do not meet the criteria of this invention. The catalysts of Examples 4 and 5 exhibit significantly different behavior than the iridium catalyst of Example 3, thus, supporting the conclusion drawn from Examples 1 and 2 that all Group VIII metals are not equivalent for ring opening activity and selectivity. Second, although more ring opening activity is observed with the iridium-containing catalyst of Example 3, the relatively high acidity of the dealuminated Y zeolite support caused sufficient degradation of the feed and primary products to reduce ring opening selectivity below the minimum range of criteria of the present invention.

Example 6
0.9 wt. % Ir/ECR-32 (Si:Al=66)

A catalyst illustrating this invention was prepared in the following manner.

Part A. A support material comprising a zeolite (an ECR-32) was prepared as described in U.S. Pat. No. 4,931, 267 incorporated herein by reference. This material had an Si/Al=5.7, a unit cell of 24.46 Å, a crystallinity=106% (compared to a standard NaY), a hexane sorption capacity of 20.6 wt. % and was shown by powder X-ray diffraction to be substantially pure ECR-32. This material was then steam-calcined for 5 hours at 675° C. (1250° F.), after which treatment the unit cell was 24.28 Å and crystallinity 98%. This steamed material was then acid exchanged and aluminum extracted in a 0.5N hydrochloric acid solution. The product was filtered, washed chloride free and analyzed. Compared to the NaY standard, X-ray diffraction showed a crystallinity of 103% and n-hexane sorption was 20.4 wt % at 45 torr and 23° C. The unit cell was 24.30 Å and chemical analysis (ICPAES) gave Si/Al=66.2.

Part B. Onto this modified ECR-32 zeolitic material was impregnated Ir metal in the following manner. The support, 48.7 g of ECR-32 (Si:Al=66), was dried in a 120° C. oven prior to incipient wetness impregnation. Wettability was determined to be 0.6 mL/g (48.7 g support requires 29.2 mL aqueous metal-containing solution). From standard solution of chloroiridic acid containing 0.1204 g/mL of Ir, 3.67 mL was added to 25.5 mL of distilled water. The resulting solution was added to the support at once with constant stirring to assure homogeneous distribution of the metal. After stirring for 20 minutes, the impregnated material was dried in a 120° C. oven overnight. The dried material was calcined (in air) wherein the temperature was ramped at 1° C./min from room temperature to the final calcination temperature, 270° C.

A portion of powdered metal-containing catalyst was mixed with 0.5 parts reforming grade alumina and formed into small catalyst particles. This catalyst was tested for selective ring-opening as described for Example 1, and the results are shown in Table 3 below. This catalyst containing iridium and a modified acidity support material meets the most preferred criteria of this invention for selective ring opening.

TABLE 3

Ring Opening Activity and Selectivity for the Catalyst of Example 6 with Comparison to the Results from Example 1

| Example | Catalyst | Temp °C. | Tot. LHSV | BCH Conv. | % $C_{10}$ RD | % $C_{10}$ PY | Selectivity |
|---|---|---|---|---|---|---|---|
| 6a | 0.9% Ir/ | 275 | 8.6 | 91.7 | 76.0 | 47.2 | 0.62 |
| 6b | ECR-32 | 275 | 12.8 | 85.7 | 63.9 | 40.9 | 0.64 |
| 6c | (Si:Al = 66) | 250 | 12.8 | 56.8 | 42.5 | 19.4 | 0.46 |
| 6d |  | 275 | 4.3 | 98.5 | 89.8 | 39.7 | 0.44 |
| 1 | 0.9% Ir/ $Al_2O_3$ | 275 | 6.0 | 38.4 | 35.2 | 13.6 | 0.39 |

These results clearly show that the catalyst of Example 6 meets the most preferred criteria of this invention for selective ring opening, and at a range of operating conditions. By comparison to the results of Example 1, it can be clearly seen that incorporating a material having an effective amount of acidity, ECR-32 (Si:Al=66), dramatically improves the performance of iridium for selective ring opening (higher $C_{10}$ paraffin yields; high selectivity at high conversion).

Example 7

0.9 wt. % Pt/ECR-32 (Si:Al=51)—Comparative

A zeolitic support material was prepared in a manner similar to that for Example 6, Part A. The prepared material was very similar in physical properties to that shown in Example 6, with a unit cell size of 24.29 and Si:Al=51. This zeolitic support was impregnated with a stock platinum solution in a manner similar to that described in Example 6, Part B.

This catalyst was tested for selective ring-opening as described for Example 6, and the results are shown in Table 4 below. This catalyst does not meet the minimum range of criteria of the present invention, and thus is not a catalyst of this invention.

TABLE 4

Comparison of Ring Opening Activity and Selectivity for Catalysts of Examples 6 and 7

| Example | Catalyst | Temp °C. | Tot. LHSV | BCH Conv. | % $C_{10}$ RD | % $C_{10}$ PY | Selectivity |
|---|---|---|---|---|---|---|---|
| 6 | 0.9% Ir/ ECR-32 (Si:Al = 66) | 275 | 8.6 | 91.7 | 76.0 | 47.2 | 0.62 |

TABLE 4-continued

Comparison of Ring Opening Activity and Selectivity for Catalysts of Examples 6 and 7

| Example | Catalyst | Temp °C. | Tot. LHSV | BCH Conv. | % $C_{10}$ RD | % $C_{10}$ PY | Selectivity |
|---|---|---|---|---|---|---|---|
| 7 | 0.9% Pt/ ECR-32 (Si:Al = 51) | 275 | 2.9 | 90.0 | 64.0 | 0.6 | 0.01 |

These results further illustrate the differences observed between iridium and platinum as selective ring opening catalysts. Even on a preferred modified acidity support material, the platinum catalyst of Example 7 fails to meet the minimum range of criteria for catalysts of the present invention, while the catalyst of Example 6, containing iridium and on a similar acidic support, meets the most preferred criteria of this invention for selective ring opening.

Examples 8–10 illustrate the capability to meet the criteria of this invention for selective ring opening through the use of physical mixtures of metal and modified acidity materials as catalysts.

Example 8

0.9 wt. % Pt/ECR-32 (Si:Al=66) Mixed with 0.9 wt. % Ir/$Al_2O_3$ (0.25:1 Weight Ratio)

Catalysts of Example 7 and Example 1 (0.8 g) were physically mixed in the ratio of one part-to-four parts, respectively, and tested for selective ring-opening as described for Example 1. The results are shown in Table 5. This catalyst containing a mixture of an indium and a catalyst modified acidity material meets the preferred criteria of this invention for selective ring opening.

Example 9

0.9 wt. % Ir/ECR-32 (Si:Al=66) Mixed with 0.9 wt. % Ir/$Al_2O_3$ (0.25:1 Weight Ratio)

Catalysts of Example 6 and Example 1 (0.8 g) were physically mixed in the ratio of one part-to-four parts, respectively, and tested for selective ring-opening as described for Example 1 The results are shown in Table 5 below. This catalyst system containing a first catalyst comprised of iridium on a low acidity support and a second catalyst containing a modified acidity support material meets the most preferred criteria of this invention for selective ring opening.

Example 10

0.9 wt. % Ir/ECR-32 (Si:Al=66) Mixed with 0.9 wt. % Ir/$Al_2O_3$ (1:1 Weight Ratio)

Equivalent parts of catalysts of Example 6 and Example 1 (0.8 g) were physically mixed and tested for selective ring-opening as described for Example 1. The results are shown in Table 5 below.

TABLE 5

Comparison of Ring Opening Activity and Selectivity for Catalysts of Examples 8, 9, 10 and 1

| Example | Ratio M/ ECR-32(66) to 0.9% Ir/ $Al_2O_3$ | Temp °C. | Tot. LHSV | BCH Conv. | % $C_{10}$ RD | % $C_{10}$ PY | Selectivity |
|---|---|---|---|---|---|---|---|
| 8 | 0.25:1 (M = 0.9 Pt) | 275 | 11.3 | 39.8 | 21.0 | 15.9 | 0.76 |

TABLE 5-continued

Comparison of Ring Opening Activity and
Selectivity for Catalysts of Examples 8, 9, 10 and 1

| Example | Ratio M/ECR-32(66) to 0.9% Ir/Al$_2$O$_3$ | Temp °C. | Tot. LHSV | BCH Conv. | % C$_{10}$ RD | % C$_{10}$ PY | Selectivity |
|---|---|---|---|---|---|---|---|
| 9 | 0.25:1 (M = 0.9 Ir) | 275 | 13.3 | 51.9 | 34.4 | 24.0 | 0.70 |
| 10 | 1:1 (M = 0.9 Ir) | 275 | 7.5 | 91.3 | 66.6 | 41.8 | 0.63 |
| 1 | 0.9% Ir/Al$_2$O$_3$ | 275 | 6.0 | 38.4 | 35.2 | 13.6 | 0.39 |

These results demonstrate that the effective metal component for selective ring opening does not have to be supported on an effective modified acidity component, rather that physical mixtures can also provide selective ring opening to meet the criteria of this invention. Example 8 illustrates that a physical mixture of the catalysts of Examples 7 and 1 provide improved ring opening activity and selectivity to meet preferred criteria of this invention, even though the catalyst of Example 1 alone meets only the minimum criteria and the catalyst of Example 7 alone does not meet the minimum criteria of this invention. Replacing the platinum catalyst of Example 8 with an iridium catalyst in Example 9 gives a significant increase ring opening activity leading to enhanced C$_{10}$ paraffin yield. Example 10 shows an even greater enhancement in C$_{10}$ paraffin yield when a greater portion of the iridium-impregnated modified acid component is used.

Example 11

0.9 wt. % Ir/amorphous SiO$_2$—Al$_2$O$_3$ (85-15)

A catalyst was prepared in a similar manner to that described in Example 1 except that the support was an amorphous silica-alumina (85:15) material prepared via methods well known in the art.

This catalyst was tested for selective ring-opening as described for Example 1. The results, by comparison with Example 1 in Table 6 below, show that this catalyst of Example 11 is similar in ring opening activity and selectivity to the catalyst of Example 1. In spite of the marginally lower than 5.0 LHSV used in Example 11, it should be obvious to one skilled in the art that this catalyst does meet the minimum range of criteria for selective ring opening of the present invention.

TABLE 6

Comparison of Ring Opening Activity and
Selectivity for Catalysts of Examples 11 and 1

| Example | Catalyst | Temp °C. | Tot. LHSV | BCH Conv. | % C$_{10}$ RD | % C$_{10}$ PY | Selectivity |
|---|---|---|---|---|---|---|---|
| 1 | 0.9% Ir/Al$_2$O$_3$ | 275 | 6.0 | 38.4 | 35.2 | 13.6 | 0.39 |
| 11 | 0.9% Ir/SiO$_2$—Al$_2$O$_3$ (85-15) | 275 | 4.2 | 42.2 | 36.7 | 16.5 | 0.45 |

Examples 12 and 13 provide a comparison of 0.9 wt. % Ir/Al$_2$O$_3$ and a physical mixture of 0.9 wt. % Ir/Al$_2$O$_3$ & 0.9 wt. % Pt/ECR-32 (Si:Al=200) for the ring opening activity and selectivity on a feedstock containing a high proportion of cyclic molecules.

Preparation of Saturated Cyclic Feedstock

An aromatics solvent stream containing primarily C$_{11}$ and C$_{12}$ naphthalenes with the composition shown in Table 7, was hydrogenated over 180 g or 250 cc of a commercially available 0.6 wt. % Pt/Al$_2$O$_3$ catalyst. The catalyst was prereduced in flowing hydrogen at 750° for 16 hours at atmospheric pressure. The aromatics solvent feedstock was passed over the catalyst at 1800 PSIG, 550° F., an LHSV of 0.5 with a hydrogen treat gas rate of 7000 SCF/B. The saturated product collected was combined and analyzed to contain less than 0.1 wt. % aromatics at the composition shown in Table 7.

TABLE 7

Composition of the Aromatics Solvent stream and the
saturated product of that stream used as a
Saturated Cyclic Feedstock in Examples 12 and 13

|  | Aromatics Solvent | Saturated Product |
|---|---|---|
| API Gravity | 10.0 | 31.6 |
| Carbon Number Distribution (approx.) | | |
| % C$_9$- molecules | <1.0 | <1.0 |
| % C$_{10}$+ molecules | >99.0 | >99.0 |
| Aromatics/Saturates Distribution | | |
| % Total Aromatics | 99.0 | <0.1 |
| % 1-ring aromatics | 11.0 | 0 |
| % 2-ring aromatics | 89.0 | 0 |
| % Paraffins | <1.0 | 1.1 |
| % C$_{10}$+ 1 ring naphthenes | <1.0 | 18.9 |
| % C$_{10}$+ 2-ring naphthenes | <1.0 | 80.0 |

All % are by weight based on the total weight of the stream.

Example 12

The catalyst of Example 1, 6.0 cc or 4.50 g, was loaded into a tubular stainless steel reactor. The catalyst was prereduced in flowing hydrogen at 350° C. for 16 hours at atmospheric pressure. The saturated feedstock prepared by the above procedure was passed over this catalyst at the conditions shown in Table 8. The results in Table 8 also show a decrease in number of cyclic structures, increase in API gravity (lower density) and increase in C$_{10}$+ paraffins versus the feed.

Example 13

A catalyst comprised of 0.9 wt. % Pt/ECR-32 (Si:Al=199) was prepared in a manner similar to that described in Example 6, except that the zeolite was finally treated with a 1.0N HCl solution rather than a 0.5N HCl solution. The resulting material had a unit cell size of 24.27 Å and a n-hexane sorption capacity of 20.4 wt %. The $^{27}$Al NMR spectrum showed a single peak at −58 ppm, indicative of only tetrahedral (framework) alumina. Chemical analysis (ICPAES) gave Si/Al=199. Chloroplatinic acid was used for the metal impregnation step. A 0.5 cc portion of this catalyst was physically mixed with 6.0 cc or 4.50 g of the catalyst of Example 1. This catalyst mixture was loaded into a tubular stainless steel reactor. The catalyst was prereduced in flowing hydrogen at 350° C. for 16 hours at atmospheric pressure. The saturated cyclic feedstock was passed over this catalyst mixture at the conditions shown in Table 8. The results in Table 8 also show a decrease in number of cyclic structures, increase in API gravity (lower density) and increase in C$_{10}$+ paraffins versus the feed.

TABLE 8

Comparison of catalysts of Examples 12 and 13 for Ring Opening of a Saturated Cyclic Feedstock

| Reactor Conditions: | Example 12 | Example 13 |
|---|---|---|
| 650 PSIG, 0.5 LHSV | (Ir only) | (Ir + ECR-32(199)) |
| API Gravity at Temp, °C./°F. | | |
| 302/575 | 33.4 | 35.3 |
| 314/598 | 34.8 | 38.7 |
| 329/625 | 36.2 | 45.4 |
| Liquid Product Analysis for 625° F. Samples | | |
| $C_9$- paraffins/naphthenes | 1.9 | 12.6 |
| $C_{10}^+$ paraffins | 4.3 | 19.6 |
| $C_{10}^+$ 1-ring naphthenes | 42.6 | 45.9 |
| $C_{10}^+$ 2-ring naphthenes | 51.1 | 21.8 |

From the results in Table 8, it can be seen that the mixture containing a portion of modified acidity material coupled with the Ir metallic catalyst in Example 12 produced superior results to that for just the metallic catalyst of Example 13.

Examples 14 and 15 provide a comparison of 0.9 wt. % Ir/$Al_2O_3$ and a commercial 0.5 wt. % Pd/USY-$Al_2O_3$ (80-20) hydrocracking catalyst for the ring opening activity and selectivity on a feedstock containing a high proportion of cyclic molecules.

Example 14
Ring Opening Activity and Selectivity of 0.9% Ir/$Al_2O_3$ on a Saturated Cyclic Feedstock A catalyst of this invention, as described in Example 1, was tested for ring opening on a saturated cyclic feedstock prepared in the manner described for the above set of examples. The properties of this saturated cyclic feedstock, FS-14, are shown in Table 9 below. A 3.91 g (6.0 mL) portion 14–35 mesh particles of the catalyst of Example 1 was mixed with 4.0 mL inert diluent particles and loaded into a stainless steel reactor. The catalyst was prereduced in flowing hydrogen (150 mL/min) at 650 PSIG under the following conditions: heat to 150° C. at 38° C./hour; hold at 150° C. for 13 hours; heat to 350° C. at 100° C./hour; hold at 350° for 17 hours. The saturated cyclic feedstock, FS-14, was passed over this catalyst mixture at the conditions shown in Table 10 below. The results in Table 10 show a decrease in number of cyclic 2-ring structures versus the relative boiling point conversion, which represents molecular weight reduction and cracking.

Example 15
Ring Opening Activity and Selectivity of 0.5 wt. % Pd/USY-$Al_2O_3$ (80-20) on a Saturated Cyclic Feedstock A commercial hydrocracking catalyst comprised of about 0.5 wt. % Pd supported on USY-$Al_2O_3$ (80-20) extrudates was tested for ring opening on a saturated cyclic feedstock prepared in the manner described in Examples 12 and 13 above. The properties of this saturated cyclic feedstock, FS-15, are shown in Table 9 below. A 0.63 g (1.0 mL) portion of 14–35 mesh particles of the hydrocracking catalyst was mixed with 9.0 mL inert diluent particles and loaded into a stainless steel reactor. The catalyst was prereduced in flowing hydrogen (150 mL/min) at 650 PSIG under the following conditions: heat to 150° C. at 25° C./hour; hold at 150° C. for 9.5 hours; heat to 300° C. at 25° C./hour; hold at 300° C. for 10 hours. The saturated cyclic feedstock, FS-15, was passed over this catalyst mixture at the conditions shown in Table 10 below. The results in Table 10 show a decrease in number of cyclic 2-ring structures versus the relative boiling point conversion, which represents molecular weight reduction and cracking.

TABLE 9

Composition of Saturated Cyclic Feedstocks used in Examples 14 and 15

| | FS-14 Example 14 | FS-15 Example 15 |
|---|---|---|
| API Gravity | 31.1 | 31.5 |
| Aromatics, by SFC | 0.5 | 1.7 |
| Sulfur, ppm | 0.06 | 0.1 |
| Nitrogen, ppm | 0.1 | 0.9 |
| Boiling Range by GC Distillation | | |
| % Boiling at °F. | | |
| 0.5 | 359 | 326 |
| 5 | 386 | 376 |
| 10 | 398 | 389 |
| 30 | 417 | 404 |
| 50 | 428 | 414 |
| 70 | 445 | 432 |
| 90 | 478 | 475 |
| 99.9 | 550 | 556 |
| % Paraffins | 1 | 1 |
| % $C_{10}^+$ 1 ring naphthenes | 17 | 17 |
| % $C_{10}^+$ 2-ring naphthenes | 82 | 82 |

TABLE 10

Comparison of Ring Opening Activity and Selectivity for Catalysts of Examples 14 and 15 (hydrogen treat gas rate held constant at 3000 SCF/B)

| Example | Catalyst | Temp °C. | Tot. LHSV | PSIG | Mole % 2-Rings | Total Liquid Product 375° F. + Conv. |
|---|---|---|---|---|---|---|
| 14a | 0.9% Ir/$Al_2O_3$ | 325 | 0.5 | 650 | 55.8 | 13.4 |
| 15a | 0.5% Pd/ USY-$Al_2O_3$ (80-20) | 275 | 5.0 | 650 | 57.6 | 37.8 |
| 14b | 0.9% Ir/$Al_2O_3$ | 350 | 0.5 | 650 | 33.1 | 29.0 |
| 15b | 0.5% Pd/ USY-$Al_2O_3$ (80-20) | 314 | 5.0 | 650 | 37.1 | 59.5 |
| 14c | 0.9% Ir/$Al_2O_3$ | 350 | 0.5 | 1000 | 8.3 | 58.9 |

Comparing Examples 14a and 15a reveal that for similar conversion levels of 2-ring molecules in the feedstock, the level of boiling range conversion is significantly less for the iridium catalyst of Example 14 than for the hydrocracking catalyst of Example 15.

Comparing Examples 14b and 15b also reveal that for higher, but also similar conversion levels of 2-ring molecules in the feedstock, the level of boiling range conversion is significantly less for the iridium catalyst of Example 14 than for the catalyst of Example 15.

Example 14c shows the high degree of 2-ring conversion possible over the iridium catalyst of Example 14 at a similar level of boiling range conversion to that for the catalyst of Example 15b.

Thus, the catalyst of Example 14, a catalyst of this invention, exhibits greater selectivity for 2-ring conversion versus boiling range conversion (overall reduction) than a hydrocracking-type catalyst.

The preferred mode of this invention is to employ a catalyst containing an effective amount of acidity, which is believed to isomerize $C_6$ to $C_5$ cycloparaffins, thus improving the activity and selectivity of the metal hydrogenolysis component of the catalyst. The following examples illustrate that iridium, ruthenium and rhodium are effective and selective ring opening catalysts for $C_5$ ring compounds. The hydrogenolysis metals of Examples 16, 17 and 18, when combined with an effective acidity component of this invention, form catalyst systems which are capable of ring opening activity and selectivity to be considered catalysts of the present invention.

Example 16
Selective Ring Opening of n-pentylcyclopentane (PCP) with 0.9 wt. % $Ir/Al_2O_3$ A portion, 0.5 g (1.0 mL), of the 0.9 wt. % $Ir/Al_2O_3$ catalyst from Example 1 was tested for selective ring-opening of n-pentylcyclopentane. A feedstock was prepared by dissolving 20 wt. % n-pentylcyclopentane, PCP, in heptane. The feedstock was then tested in a manner similar to that described for BCH in the Catalyst Selection Procedure above. The results of this test are shown in Table 11 below, wherein the %$C_{10}$ paraffin yield and selectivity, defined by %$C_{10}$ paraffin yield/%$C_{10}$ ring disappearance, were determined by a method similar to that for BCH described previously. The ring opening activity and selectivity of the 0.9 wt. % $Ir/Al_2O_3$ catalyst for this $C_5$ ring compound is extremely high, thus illustrating that when combined with an effective acidity component of this invention, iridium can form a catalyst system which are capable of ring opening activity and selectivity to be considered catalysts of the present invention.

Example 17
Selective Ring Opening of PCP with 0.5 wt. % $Ru/A_2O_3$

A commercial ruthenium on alumina catalyst, a 0.75 g (1.0 mL) portion, was tested for selective ring-opening as described for Example 16. The results are shown in Table 11 and illustrate that this ruthenium catalyst also exhibits high ring opening activity and selectivity for this $C_5$ ring compound. Further, these results illustrate that when combined with an effective acidity component of this invention, ruthenium can form catalyst systems which are capable of ring opening activity and selectivity to be considered catalysts of the present invention.

Example 18
Selective Ring Opening of n-Pentylcyclopentane with 0.5 wt. % $Rh/Al_2O_3$ A commercial rhodium on alumina catalyst, a 0.71 g (1.0 mL) portion, was tested for selective ring-opening as described for Example 16. The results are shown in Table 11 and illustrate that this rhodium catalyst also exhibits high ring opening activity and selectivity for this $C_5$ ring compound. Further, these results illustrate that when combined with an effective acidity component of this invention, rhodium can form catalyst systems which are capable of ring opening activity and selectivity to be considered catalysts of the present invention.

TABLE 11

Comparison of n-Pentylcyclopentane Ring Opening Activity and Selectivity for Catalysts of Examples 16, 17 and 18

| Example | Catalyst | Temp °C. | Tot. LHSV | PCP Conv. | % $C_{10}$ RD | % $C_{10}$ PY | Select-ivity |
|---|---|---|---|---|---|---|---|
| 16 | 0.9% Ir/$Al_2O_3$ | 250 | 5.0 | 65.0 | 65.0 | 59.8 | 0.92 |
| 17 | 0.5% Ru/$Al_2O_3$ | 225 | 5.0 | 44.0 | 44.0 | 36.1 | 0.82 |
| 18 | 0.5% Rh/$Al_2O_3$ | 275 | 5.0 | 68.3 | 68.3 | 59.3 | 0.87 |

These results illustrate that, when combined with an effective acidity component of this invention to form $C_5$ cycloparaffins via isomerization of $C_6$ rings, iridium, ruthenium and rhodium are capable of selective ring opening activity and selectivity.

What is claimed is:

1. A process for selectively opening rings of ring compounds in a feedstream wherein at least about 50 wt. % of the ring compounds in the feedstream are characterized as containing at least one $C_6$ ring having at least one substituent containing 3 or more carbon atoms, which substituents are selected from the group consisting of fused 5-membered rings; fused 6-membered rings; $C_3$ or greater alkyls, cycloalkyls; and aryl groups, which process comprises contacting said feedstream with
a catalyst component in the presence of hydrogen at a temperature from about 150° C. to about 400° C., a total pressure of 0 to 3,000 psig, which catalyst is comprised of an effective amount of a metal selected from Ir, Ru, Rh or mixtures thereof, on a catalyst support, which catalyst when reacted with a feed comprised of 20 wt. % n-butylcyclohexane in heptane diluent, at a temperature of 150° C. to 350° C., a hydrogen treat rate of 2,000 standard cubic feet per barrel on liquid feed, a total pressure of 500 psig, and a liquid hourly space velocity of at least 5 on liquid feed, will result in: a) at least a 10% yield of $C_{10}$ paraffins; and b) a selectivity of at least 0.20, which selectivity is defined as %$C_{10}$ paraffin yield/%$C_{10}$ ring disappearance.

2. The process of claim 1 wherein the amount of metal of the catalyst is up to about 10 wt. %, based on the total weight of the catalyst.

3. The process of claim 2 wherein the amount of metal is from about 0.01 to about 3 wt. %, based on the total weight of the catalyst.

4. The process of claim 3 wherein the catalyst, when reacted with the 20 wt. % n-butylcyclohexane in heptane diluent, will result in: a) at least a 15% yield of $C_{10}$ paraffins: and b) a selectivity of at least 0.30.

5. The process of claim 4 wherein the catalyst, when reacted with the 20 wt. % n-butylcyclohexane in heptane diluent, will result in: a) at least a 20% yield of $C_{10}$ paraffins: and b) a selectivity of at least 0.40.

6. The process of claim 3 wherein the amount of metal is from about 0.1 to 1 wt. %, based on the total weight of the catalyst.

7. The process of claim 3 wherein the metal is Ir.

8. The process of claim 1 wherein the catalyst also contains an effective amount of one or more performance enhancing transition metals.

9. The process of claim 8 wherein the one or more performance enhancing transition metals is selected from the 4th, 5th, and 6th periods of the Periodic Table of the Elements.

10. The process of claim 9 wherein the catalyst, when reacted with the 20 wt. % n-butylcyclohexane in heptane diluent, will result in: a) at least a 15% yield of $C_{10}$ paraffins: and b) a selectivity of at least 0.30.

11. The process of claim 10 wherein the catalyst, when reacted with the 20 wt. % n-butylcyclohexane in heptane diluent, will result in: a) at least a 20% yield of $C_{10}$ paraffins: and b) a selectivity of at least 0.40.

12. The process of claim 1 wherein the catalyst support contains an acidic function.

13. The process of claim 12 wherein the support material is selected from alumina, silica, and alumina-silica which has been modified to have an effective acidic function.

14. The process of claim 12 wherein the support material contains a zeolitic material having an effective amount of acidic function.

15. The process of claim 14 wherein the zeolitic material is characterized as:

having an Si/M atomic ratio greater than about 30, said material being derived from a faujasite and having a structure characteristic of faujasite having an "as synthesized" Si/M atomic ratio greater than about 4, wherein M is Al, Ga, B, Zn, Fe or Cr cation, or mixtures thereof.

16. The process of claim 12 wherein the catalyst, when reacted with the 20 wt. % n-butylcyclohexane in heptane diluent, will result in: a) at least a 15% yield of $C_{10}$ paraffins: and b) a selectivity of at least 0.30.

17. The process of claim 16 wherein the catalyst, when reacted with the 20 wt. % n-butylcyclohexane in heptane diluent, will result in: a) at least a 20% yield of $C_{10}$ paraffins: and b) a selectivity of at least 0.40.

18. A process for selectively opening rings of ring compounds in a feedstream wherein at least about 50 wt. % of the ring compounds in the feedstream are characterized as containing at least one $C_6$ ring having at least one substituent containing 3 or more carbon atoms, which substituents are selected from the group consisting of fused 5-membered rings; fused 6-membered rings; $C_3$ or greater alkyl or cycloalkyl groups; and aryl groups, which process comprises contacting said feedstream with a catalyst component in the presence of hydrogen at a temperature from about 150° C. to about 400° C., a total pressure of 0 to 3000 psig, which catalyst is comprised of an effective amount of Ir on a catalyst support having an acidity to promote isomerization, which catalyst when reacted with a feed comprised of 20 wt. % n-butylcyclohexane in heptane diluent, at a temperature of 150° C. to 350° C., a hydrogen treat rate of 2,000 standard cubic feet per barrel on liquid feed, a total pressure of 500 psig, and a liquid hourly space velocity of at least 5 on liquid feed, will result in: a) at least a 15% yield of $C_{10}$ paraffins: and b) a selectivity of at least 0.30, which selectivity is defined as %$C_{10}$ paraffin yield/%$C_{10}$ ring disappearance.

19. The process of claim 18 wherein the support material contains a zeolite having an effective amount of acid function, which zeolite is characterized as:

having an Si/M atomic ratio greater than about 30, said material being derived from a faujasite and having a structure characteristic of faujasite having an "as synthesized" Si/M atomic ratio greater than about 4, wherein M is Al, Ga, B, Zn, Fe or Cr cation, or mixtures thereof.

20. The process of claim 18 wherein at least one performance enhancing transition metal is present on said catalyst, which one or more metals is selected from the 4th, 5th, and 6th periods of the Periodic Table of the Elements.

21. The process of claim 18 wherein the catalyst, when reacted with the 20 wt. % n-butylcyclohexane in heptane diluent, will result in: a) at least a 20% yield of $C_{10}$ paraffins: and b) a selectivity of at least 0.40.

22. The process of claim 18 wherein the catalyst is a catalyst system containing a first and a second catalyst, the first catalyst being comprised of Ir on a substantially non-acidic support, and a second catalyst comprised of a material having an effective acidic function.

23. The process of claim 22 wherein the substantially non-acidic support is an alumina.

24. The process of claim 23 wherein the second catalyst contains a zeolite characterized as:

having an Si/M ratio greater than about 30, said material being derived from a faujasite and having a structure characteristic of faujasite having an "as synthesized" Si/M atomic ratio greater than about 4, wherein M is Al, Ga, B, Zn, Fe or Cr cation, or mixtures thereof.

25. The process of claim 24 wherein M is Al.

26. The process of claim 19 wherein M is Al.

27. A two stage process for selectively opening rings of ring compounds in a feedstream wherein at least about 50 wt. % of the ring compounds in the feedstream are characterized as containing at least one $C_6$ ring having at least one substituent containing 3 or more carbon atoms, which substituents are selected from the group consisting of fused 5-membered rings, fused 6-membered rings, $C_3$ or greater alkyl or cycloalkyl groups and aryl groups, which process comprises:

contacting said feedstream in a first reaction zone with a first catalyst containing an acidic function effective to promote isomerization without an undesirable level of severance of any substituent groups on the ring;

passing the so-treated feedstream to a second reaction zone where it is contacted with a second catalyst in the presence of hydrogen at a temperature from about 150° C. to about 400° C., a total pressure of 0 to 1200 psig, which second catalyst is comprised of an effective amount of a metal selected from Ir, Ru, or a mixture thereof, on a catalyst support which is substantially non-acidic, which catalyst when reacted with a feed comprised of 20 wt. % n-butylcyclohexane in heptane diluent, at a temperature of 150° C. to 350° C., a hydrogen treat rate of 2,000 standard cubic feet per barrel on liquid feed, a total pressure of 500 psig, and a liquid hourly space velocity of at least 5 on liquid feed, will result in: a) at least a 10% yield of $C_{10}$ paraffins: and b) a selectivity of at least 0.20, which selectivity is defined as %$C_{10}$ paraffin yield/%$C_{10}$ ring disappearance.

28. The process of claim 27 wherein the feedstream is in the distillate boiling range and the second catalyst contains up to about 10 wt. % metal, based on the total weight of the catalyst.

29. The process of claim 28 wherein the amount of metal is from about 0.01 to about 3 wt. %, based on the total weight of the catalyst.

30. The process of claim 29 wherein the catalyst, when reacted with the 20 wt. % n-butylcyclohexane in heptane diluent, will result in: a) at least a 15% yield of C10 paraffins; and b) a selectivity of at least 0.30.

31. The process of claim 30 wherein the catalyst, when reacted with the 20 wt. % n-butylcyclohexane in heptane diluent, will result in: a) at least a 20% yield of $C_{10}$ paraffins; and b) a selectivity of at least 0.40.

32. The process of claim 29 wherein the amount of metal is from about 0.1 to 1 wt. %, based on the total weight of the catalyst.

33. The process of claim 29 wherein the metal is Ir.

34. The process of claim 27 wherein either the first catalyst, or the second catalyst contains an effective amount of at least one performance enhancing transition metal.

35. The process of claim 34 wherein the one or more performance enhancing transition metals is selected from the 4th, 5th, and 6th periods of the Periodic Table of the Elements.

36. The process of claim 35 wherein the catalyst, when reacted with the 20 wt. % n-butylcyclohexane in heptane diluent, will result in: a) at least a 15% yield of $C_{10}$ paraffins; and b) a selectivity of at least 0.30.

37. The process of claim 36 wherein the catalyst, when reacted with the 20 wt. % n-butylcyclohexane in heptane diluent, will result in: a) at least a 20% yield of $C_{10}$ paraffins; and b) a selectivity of at least 0.40.

38. The process of claim 27 wherein the first catalyst is selected from alumina, silica, and alumina-silica which has been modified to have an effective acidic function.

39. The process of claim 38 wherein the first catalyst contains a zeolite having an effective amount of acidic function.

40. The process of claim 39 wherein the zeolite is characterized as: having an Si/M atomic ratio greater than about 30, said material being derived from a faujasite and having a structure characteristic of faujasite having an "as synthesized" Si/M atomic ratio greater than about 4, wherein M is Al, Ga, B, Zn, Fe or Cr cation, or mixtures thereof.

41. The process of claim 40 wherein M is Al.

42. The process of claim 40 wherein the catalyst, when reacted with the 20 wt. % n-butylcyclohexane in heptane diluent, will result in: a) at least a 15% yield of $C_{10}$ paraffins; and b) a selectivity of at least 0.30.

43. The process of claim 42 wherein the catalyst, when reacted with the 20 wt. % n-butylcyclohexane in heptane diluent, will result in: a) at least a 20% yield of $C_{10}$ paraffins; and b) a selectivity of at least 0.40.

* * * * *